(12) United States Patent
Boyer et al.

(10) Patent No.: US 8,158,776 B2
(45) Date of Patent: *Apr. 17, 2012

(54) P2Y$_6$ RECEPTOR AGONISTS FOR TREATING LUNG DISEASES

(75) Inventors: José L. Boyer, Chapel Hill, NC (US); Sammy R. Shaver, Chapel Hill, NC (US); James G. Douglass, III, Apex, NC (US); Catherine C. Redick, Durham, NC (US)

(73) Assignee: Inspire Pharmaceuticals, Inc., Whitehouse Station, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/939,934

(22) Filed: Nov. 4, 2010

(65) Prior Publication Data
US 2011/0054163 A1    Mar. 3, 2011

Related U.S. Application Data

(63) Continuation of application No. 11/478,338, filed on Jun. 28, 2006, now Pat. No. 7,851,456.

(60) Provisional application No. 60/695,358, filed on Jun. 29, 2005.

(51) Int. Cl.
*C07H 19/04*    (2006.01)
*C07H 19/20*    (2006.01)

(52) U.S. Cl. .......... 536/26.26; 536/26.1; 536/26.2; 536/26.21

(58) Field of Classification Search .......... None
See application file for complete search history.

(56) References Cited

U.S. PATENT DOCUMENTS 7,851,456 B2 * 12/2010 Boyer et al. .......... 514/47
* cited by examiner

*Primary Examiner* — Traviss C McIntosh, III
(74) *Attorney, Agent, or Firm* — Perkins Coie LLP.; Viola T. Kung

(57) ABSTRACT

This invention is directed to a method of enhancing or facilitating the clearance or the lung mucus secretions in a subject. This invention is also directed to a method of facilitating the hydration of the lung mucus secretions in a subject. This invention is further directed to a method of preventing or treating diseases or conditions associated with impaired lung or airway function in a human or other mammal. The method comprises administering to a subject a pharmaceutical composition comprising a therapeutic effective amount of P2Y$_6$ receptor agonist compound, wherein said amount is effective to activate the P2Y$_6$ receptors on the luminal surface of lung epithelia. The P2Y$_6$ receptor agonist compounds useful for this invention include mononucleoside 5'-diphosphates, dinucleoside monophosphate, dinucleoside diphosphates, or dinucleoside triphosphates of general Formula I, or salts, solvates, hydrates thereof. This invention is also directed to novel P2Y$_6$ receptor agonist compounds.

5 Claims, No Drawings

P2Y₆ RECEPTOR AGONISTS FOR TREATING LUNG DISEASES

This application is a continuation of U.S. application Ser. No. 11/478,338, filed Jun. 28, 2006, now U.S. Pat. No. 7,851,456 which claims priority to U.S. provisional application No. 60/695,358, filed Jun. 29, 2005. The content of which is incorporated herein by reference in its entirety.

TECHNICAL FIELD

This invention relates to $P2Y_6$ receptor agonists compounds and the method of using such compounds in the treatment of diseases or conditions associated with impaired lung and airway function in humans and other mammals.

BACKGROUND OF THE INVENTION

The P2 receptor subtypes $P2Y_2$, $P2Y_4$, $P2Y_6$ and the adenosine receptor subtype $A_{2B}$ are all expressed in human airways. Instillation of ATP, UTP, or UDP into the lungs produces an increase in the mucociliary clearance process in the airway epithelium. This response to extracellular nucleotides is produced by a number of events triggered by activation of one or more P2Y receptors, resulting in an increase in fluid and chloride secretion ($P2Y_2$, $P2Y_4$, and $P2Y_6$), inhibition of sodium absorption ($P2Y_2$, $P2Y_4$, and $P2Y_6$), and increase in mucin secretion ($P2Y_2$ and $P2Y_4$). These events, in concert with an increase in ciliary beat frequency, are responsible for the natural clearance of the airways. See Kellerman, *Chest.* 121:201 S-205S (2002); Knowles, *J Clin Invest.* 109:571-7 (2002); Leipziger, *Am J Physiol Renal Physiol.* 284: F419-32 (2003); Kunzelmann, *Clin Exp Pharmacol Physiol.* 28:857-67 (2001); and Schwiebert, *Biochim Biophys Acta.* 1615:7-32 (2003).

The role of $P2Y_6$ receptors has not been as clearly defined as that of $P2Y_2$ receptors and their agonists due in part to the lack of selective $P2Y_6$ agonists. Stimulation of $P2Y_6$ receptors causes a dose-dependent increase of fluid secretion, chloride secretion and ciliary beat frequency (Morse, *Am. J. Physiol. Cell Physiol.* 280:C1485-497 (2001)). UDP, the natural agonist of $P2Y_6$ receptors, has lower efficacy promoting mucociliary clearance than agonists of $P2Y_2$ receptors, whether the low efficacy of the natural $P2Y_6$ receptor agonist UDP is due to its metabolic liability is not known.

Mucus clearance is the cornerstone in the innate defense mechanism of the lung against disease produced by inhaled bacteria, viruses, chemicals and particulate material. In several lung diseases such as chronic obstructive pulmonary diseases (COPD), mucus hypersecretion, decreased clearance and inflammation contribute to airflow obstruction, resulting in destructive changes in the pulmonary parenchyma associated with an increase of morbidity and mortality. In these patients, airway clearance therapy is necessary to prevent infection, increase oxygenation and prevent progression of the decline in lung function.

SUMMARY OF THE INVENTION

This invention is directed to a method of enhancing or facilitating the clearance of the lung mucus secretions of a subject in need of such treatment. This invention is also directed to a method of facilitating the hydration of lung mucus secretion of a subject in need of such treatment. This invention is further directed to a method of preventing or treating diseases or conditions associated with impaired lung or airway function in a human or other mammal. Such diseases include chronic obstructive pulmonary disease (COPD), chronic bronchitis, emphysema, cystic fibrosis, primary ciliary dyskinesia (PCD), and alpha 1 antitrypsin deficiency.

The methods comprise administering to a subject a therapeutic effective amount of a selective $P2Y_6$ receptor agonist compound, wherein said amount is effective to activate the $P2Y_6$ receptors on the luminal surface of lung epithelia. The $P2Y_6$ receptor agonist compound, for example, is administrated to a subject by inhalation.

The $P2Y_6$ receptor agonist compounds useful for this invention are selective for $P2Y_6$ receptors, and include mononucleoside 5'-diphosphates, dinucleoside monophosphate, dinucleoside diphosphates, or dinucleoside triphosphates of general Formula I, or salts, solvates, hydrates thereof. The present invention further provides pharmaceutical formulations comprising a pharmaceutical carrier and a compound of general Formula I.

DETAILED DESCRIPTION OF THE INVENTION

Definitions

When present, unless otherwise specified, the following terms are generally defined as, but are not limited to, the following:

Alkyl groups are from 1 to 12 carbons inclusively, either straight chained or branched, with or without heteroatoms, are more preferably from 1 to 8 carbons inclusively, and most preferably 1 to 6 carbons inclusively.

Alkenyl groups are from 1 to 12 carbons inclusively, either straight or branched containing at least one double bond but may contain more than one double bond, with or without heteroatoms.

Alkynyl groups are from 1 to 12 carbons inclusively, either straight or branched containing at least one triple bond but may contain more than one triple bond, and additionally may contain one or more double bonded moieties, with or without heteroatoms.

Cycloalkyl groups are from 3 to 12 carbons inclusively, more preferably from 3 to 10 carbons inclusively, and most preferably 3 to 6 carbons inclusively, with or without heteroatoms.

Cycloalkenyl groups are from 4 to 12 carbons inclusively containing at least one double bond, and with or without heteroatoms.

Aralkyl groups are from 1 to 8 carbons inclusively in the alkyl portion, are more preferably from 1 to 6 carbons inclusively in the alkyl portion, and most preferably are 1 to 4 carbons inclusively in the alkyl portion; in addition to the alkyl definition above, the alkyl portion of an aralkyl group can include one or more positions of unsaturation such as a double bond or a triple bond in the chain when the chain includes two or more carbon atoms; the alkyl portion of an aralkyl group can also include one or more heteroatoms and/or substituents; the aryl portion of an aralkyl group can be a monocyclic or polycyclic moiety from 3 to 8 carbons inclusively per ring in the aryl portion, more preferably from 4 to 6 carbons inclusively per ring, and most preferably 5 to 6 carbons inclusively per ring; the aryl portion of an aralkyl group can also bear one or more substituents and/or heteroatoms.

Aryl groups are either monocyclic or polycyclic, are from 3 to 8 carbons inclusively per ring, are more preferably from 4 to 6 carbons inclusively per ring, and are most preferably 5 to 6 carbons inclusively per ring; aryl groups can also bear substituents and/or heteroatoms.

Heteroaralkyl groups are from 1 to 8 carbons inclusively in the alkyl portion, are more preferably from 1 to 6 carbons inclusively in the alkyl portion, and most preferably are 1 to 4 carbons inclusively in the alkyl portion; in addition to the alkyl definition above, the alkyl portion of a heteroaralkyl group can include one or more positions of unsaturation such as a double bond or a triple bond in the chain when the chain includes two or more carbon atoms; the alkyl portion of a heteroaralkyl group can also include one or more heteroatoms and/or substituents; the heteroaryl portion of a heteroaralkyl group can be a monocyclic or polycyclic moiety from 3 to 8 carbons inclusively per ring in the heteroaryl portion and containing from 1 to 4 heteroatoms inclusively per ring, more preferably from 4 to 6 carbons inclusively per ring, and most preferably 5 to 6 carbons inclusively per ring; the heteroaryl portion of an heteroaralkyl group can also bear one or more substituents and/or heteroatoms.

Heteroaryl groups are either monocyclic or polycyclic, contain from 1 to 4 heteroatoms inclusively per ring, are from 3 to 8 atoms inclusively per ring, are more preferably from 4 to 6 atoms inclusively per ring, and are most preferably 5 to 6 atoms inclusively per ring; heteroaryl groups can also bear substituents and/or heteroatoms.

Substituents on the foregoing groups can be, but are not limited to, hydroxy, nitro, methoxy, fluoro, chloro, bromo, iodo, methyl, ethyl, propyl, butyl, thioalkyl, alkoxy, carboxyl, carboxamido, alkylsulfonyl, alkylsulfonylamino, sulfonamido, cyano, amino, substituted amino, trifluoromethyl, trifluoromethoxy, phenyl, pyridyl, imidazolyl, cyclopropyl, cyclopentyl, and cyclohexyl; and preferred heteroatoms are oxygen, nitrogen, and sulfur.

A desired substituent on a chain or ring (in place of a hydrogen at a position) is one selected from the given alkyl, aryl, halogen, aralkyl, carboxy, alkoxycarbonyl, hydroxyl, acyloxy, alkoxy, aryloxy or aralkoxy classes or from other classes, which provides a compound with good-to-excellent $P2Y_{12}$ receptor-binding properties, but which does not yield a compound with undesirable properties like chemical instability in a formulation, or one with levels of toxicity that are not well-tolerated by a treated mammal, or especially, not well-tolerated by a human.

Diastereomers are stereoisomers (isomers of identical constitution but differing three-dimensional architecture), which do not bear a mirror-image relation to each other.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, mesylic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$). Other salts such as hydrochlorides, hydrobromides, mesylates, sulfates, acetates, tartrates, etc., are also contemplated in this invention. Preferred counterions are monovalent ions such as $NH_4^+$, sodium, lithium, potassium, chloride, bromide, bisulfate, and mesylate, with sodium, potassium, chloride and mesylate being most preferred due to ease of manufacture, stability, and physiological tolerance.

Solvates are addition complexes in which a compound is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N, N-dimethylformamide, N-methylacetamide, pyridine, dioxane, and diethyl ether. Hydrates are solvates in which the cosolvent is water. It is to be understood that the definition of the compound of the present invention encompasses all possible hydrates and solvates, in any proportion, which possess the stated activity.

The inventors have unexpectedly discovered a novel class of $P2Y_6$ receptor agonists, which in contrast with currently available natural or synthetic agonists, are more metabolically stable and more selective, particularly lacking of $P2Y_2$ and $P2Y_4$ receptor activity. In general, stimulation of $P2Y_6$ receptors do not cause an increase of mucin release as does stimulation of $P2Y_2$ receptors (Conway J D, *Am J Physiol. Lung Cell Mol. Physiol.* 284:L945-L954 (2003)). Applicants have discovered that certain selective $P2Y_6$ receptor agonists are particularly useful in the treatment of diseases or conditions associated with impaired or deficient airway function, where increased airway mucus production already exists and the enhancement of mucociliary clearance is desired.

This invention is directed to a method of enhancing or facilitating the clearance or removal of the lung mucus secretions of a subject in need of such treatment. Lung mucus clearance depends on an optimal balance of fluid, ions, surfactant and mucus secreted by the airways. These components of lung secretions are organized in the surface of the airways as a bilayer consisting of a top mucus layer floating on the surface of a periciliary liquid layer of approximately 7 μm thick that allows efficient cilia movement to propel the mucus layer from the lower respiratory tract to the pharynx. The mucus layer protects the epithelium from inhaled pathogens and other foreign material and from loss of fluid. The excess of mucus, the lack of fluid, and/or an imbalance of ions in the airway are hallmark characteristics associated with patients with lung diseases that contribute to compromised clearance of the lung mucus secretions, to recurrent pulmonary infections and to an overall decline in lung function associated with increases in morbidity and mortality. These patients benefit from the treatment with $P2Y_6$ agonists to promote clearance of the lungs without enhancing a mucus secretion.

This invention is also directed to a method of facilitating the hydration of lung mucus secretions of a subject in need of such treatment. This invention is further directed to a method of treating diseases or conditions associated within impaired or deficient airway function; such diseases include chronic obstructive pulmonary disease (COPD), chronic bronchitis, emphysema, chronic asthma, chronic bronchiolitis, cystic fibrosis, primary ciliary dyskinesia (PCD), and alpha 1 antitrypsin deficiency.

The method comprises administering to a subject a therapeutically effective amount of a selective $P2Y_6$ receptor agonist compound, wherein said amount is effective to bind to the $P2Y_6$ receptors on the luminal surface of airway epithelia to cause mucociliary clearance; preferably without concomitant mucin release. The compound is effective to stimulate chloride and water secretion and therefore affects an increase in the lung hydration state, with a concomitant increase in ciliary beat frequency.

Selective P2Y$_6$ Receptor Agonist Compounds

The selective P2Y$_6$ receptor agonist compounds useful for this invention have selectivity of P2Y$_6$ receptor over P2Y$_1$, P2Y$_2$, or P2Y$_4$ receptor. The selective P2Y$_6$ receptor agonist compounds useful for this invention include compounds of general Formula I, or salts, solvates, hydrates thereof:

Formula I $$A{-}O{-}\left[\begin{matrix}W\\\|\\P{-}X_2\\|\\OM\end{matrix}\right]_n\left[\begin{matrix}V\\\|\\P{-}X_1\\|\\OM\end{matrix}\right]\left[\begin{matrix}T_1\\\|\\P{-}O\\|\\OM\end{matrix}\right]_p{-}\text{(furanose-B)}$$

wherein:

B is a purine or a pyrimidine residue according to general Formulae IV or V;

n and p=0 or 1; such that the sum of n+p is from 0 to 2, and preferably 1 to 2; with the proviso that when A=M, the sum of n+p is 1;

X$_1$ and X$_2$ are independently O, NH, CH$_2$, CHF, CHCl, CF$_2$, or CCl$_2$;

T$_1$, V, and W are independently O or S;

M=H$^+$, NH$_4^+$, Na$^+$ or other pharmaceutically-acceptable inorganic or organic counter ion;

Y=OR$_1$;

Z=OR$_2$;

A=M, or

A is a nucleoside residue which is defined as:

which is linked to the phosphate chain via the 5' position of the furanose or carbocycle;

wherein: D=O or CH$_2$;

Z'=H or OH

Y'=H or OH;

B' is a purine or a pyrimidine residue according to general Formulae IV or V which is linked to the 1'-position of the furanose or carbocycle via the 9- or 1-position of the base, respectively.

R$_1$ and R$_2$ are residues that are linked directly to the 2'- and/or 3'-hydroxyls of the respective furanose or carbocycle via a carbon atom according to Formula II, or linked directly to two (2'- and 3'-)hydroxyls of the respective furanose or carbocycle via a common carbon atom according to Formula III, such that two independent residues of R$_1$ and R$_2$ falling within the definition of Formula II are present, or a combination of two independent residues made up of R$_1$+R$_2$ falling within the definition of Formula III are present;

Formula II wherein:

O is the corresponding 2'- and/or 3'-oxygen of the respective furanose or carbocycle;

C is a carbon atom;

R$_5$, R$_6$, and R$_7$ are H, alkyl, alkenyl, alkynyl, cycloalkyl, cycloalkenyl, aralkyl, aryl, substituted aralkyl, or substituted aryl, such that the moiety defined according to Formula II is an ether; or R$_5$ and R$_6$ are H, an alkyl, alkenyl, alkynyl, cycloalkyl, cycloalkenyl, aralkyl, aryl, substituted aralkyl, or substituted aryl, and R$_7$ is alkoxy, cycloalkoxy, aralkyloxy, aryloxy, substituted aralkyloxy, or substituted aryloxy such that the moiety defined according to Formula II is an acyclic acetal or ketal; or R$_5$ and R$_6$ are taken together as oxygen or sulfur doubly bonded to C, and R$_7$ is alkyl, alkenyl, alkynyl, cycloalkyl, cycloalkenyl, aralkyl, aryl, substituted aralkyl, or substituted aryl, such that the moiety defined according to Formula II is an ester or thioester; or R$_5$ and R$_6$ are taken together as oxygen or sulfur doubly bonded to C, and R$_7$ is amino or mono- or disubstituted amino, where the substituents are alkyl, alkenyl, alkynyl, cycloalkyl, cycloalkenyl, aralkyl, aryl, substituted aralkyl, or substituted aryl, such that the moiety according to Formula II is a carbamate or thiocarbamate; or R$_5$ and R$_6$ are taken together as oxygen or sulfur doubly bonded to C, and R$_7$ is alkoxy, cycloalkoxy, aralkyloxy, aryloxy, substituted aralkyloxy, or substituted aryloxy, such that the moiety according to Formula II is a carbonate or thiocarbonate; or R$_7$ is not present and R$_5$ and R$_6$ are taken together as oxygen or sulfur doubly bonded to C and both the 2'- and 3'-oxygens of the respective furanose or carbocycle are directly bound to C to form a cyclical carbonate or thiocarbonate;

Formula III wherein:

the O atoms are the 2'- and 3'-oxygens of a furanose or carbocycle; and the 2'- and 3'-oxygens of the furanose or carbocycle are linked by a common carbon atom (C) to form a cyclical acetal, cyclical ketal, or cyclical orthoester;

for cyclical acetals and ketals, R$_8$ and R$_9$ are independently hydrogen, alkyl, alkenyl, alkynyl, cycloalkyl, cycloalkenyl, aralkyl, aryl, substituted aralkyl, substituted aryl, or can be joined together to form a homocyclic or heterocyclic ring composed of 3 to 8 atoms, preferably 3 to 6 atoms;

for cyclical orthoesters, R$_8$ is hydrogen, alkyl, alkenyl, alkynyl, cycloalkyl, cycloalkenyl, aralkyl, aryl, substituted aralkyl, or substituted aryl, R$_9$ is alkyloxy, cycloalkyloxy, aralkyloxy, aryloxy, substituted aralkyloxy, or substituted aryloxy;

B and B' are independently a purine residue, as in Formula IV, linked through the 9-position, or a pyrimidine residue, as in Formula V, linked through the 1-position;

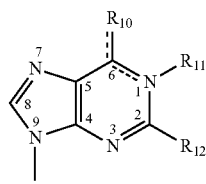

Formula IV

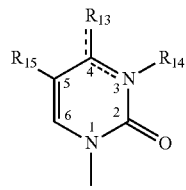

Formula V wherein:

$R_{10}$ and $R_{13}$ independently are hydroxy, oxo, amino, mercapto, alkylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or $R_{10}$ and $R_{13}$ independently are acylamino according to Formula VI;

when $R_{10}$ in a purine or $R_{13}$ in a pyrimidine has as its first atom nitrogen, $R_{10}$ and $R_{11}$ or $R_{13}$ and $R_{14}$ can be taken together to form a 5-membered fused imidazole ring (to give an etheno compound), optionally substituted on the etheno ring with one or more alkyl, alkenyl, alkynyl, cycloalkyl, cycloalkenyl, aralkyl, or aryl moieties, as described for $R_5$-$R_9$ above;

$R_{11}$ is hydrogen, O (adenine 1-oxide derivatives) or is absent (adenine derivatives);

$R_{14}$ is hydrogen, or acyl (e.g. acetyl, benzoyl, phenylacyl, with or without substituents);

$R_{12}$ is hydrogen, chlorine, amino, monosubstituted amino, disubstituted amino, alkylthio, arylthio, or aralkylthio, where the substituent on sulfur contains up to a maximum of 20 carbon atoms, with or without unsaturation, and with or without substituents on the chain;

$R_{15}$ is hydrogen, methyl, alkyl, halogen, alkyl, alkenyl, substituted alkenyl, alkynyl, or substituted alkynyl;

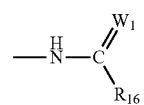

Formula VI wherein:

NH is the amino residue at the C-6 position in a purine or the amino residue at the C-4 position in a pyrimidine;

C is a carbon atom;

$W_1$ is oxygen or sulfur;

$R_{16}$ is amino or mono- or disubstituted amino, with the amino substituent(s) being alkyl, alkenyl, alkynyl, cycloalkyl, cycloalkenyl, aralkyl, or aryl, with or without further substituents, unsaturation, or heteroatoms, such that the moiety according to Formula VI is a urea or thiourea; or $R_{16}$ is alkoxy, aralkyloxy, aryloxy, substituted aralkyloxy, or substituted aryloxy, such that the moiety according to Formula VI is a carbamate or thiocarbamate; or $R_{16}$ is alkyl, alkenyl, alkynyl, cycloalkyl, cycloalkenyl, aralkyl, or aryl, with or without substituents or heteroatoms, such that the moiety according to Formula VI is an amide; with definitions of alkyl, cycloalkyl, aralkyl, or aryl groups as previously defined for comparable groups in $R_5$ to $R_9$.

When $R_5$, $R_6$ and $R_7$ are not the same, or when $R_8$ and $R_9$ are not the same, a compound according to Formula I can exist in several diastereomeric forms. The general structure of Formula I includes all diastereomeric forms of such materials, when not specified otherwise. Formula I also includes mixtures of compounds of Formula I, including mixtures of enantiomers, diastereomers and/or other isomers in any proportion.

The ribosyl moieties in Formula I are in the D-configuration as shown, but can also be L-, or D- and L-. The D-configuration is preferred for ribosyl moieties.

The Formula I compounds have the features of: (a) being a mononucleoside 5'-diphosphates, dinucleoside monophosphate, dinucleoside diphosphates, or dinucleoside triphosphates; (b) both Y=$OR_1$ and Z=$OR_2$; and (c) Y'=H or OH, and Z'=H or OH. When the compound is a dinucleotide, the polyphosphate linking the two nucleosides cannot be tetraphosphates, pentaphosphates, hexaphosphates, etc, such that the compound does not have a significant activity toward $P2Y_2$ or $P2Y_4$ receptors. When the compound is a dinucleotide, one nucleoside must have both Y and Z substituted, that is, Y and Z cannot be OH or H but must be OR; and the other nucleoside must not have either Y' or Z' substituted, that is Y' and Z' must be either OH or H, such that the compound retains the activity toward $P2Y_6$ receptors. It is those features that make the Formula I compounds have the selectivity of $P2Y_6$ receptor over other P2Y receptors.

A preferred Formula I is Formula Ia,

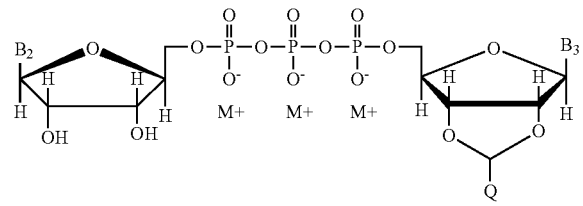

Formula Ia wherein $B_2$ and $B_3$ are independently uracil, N-methyluracil, 5-methyluracil, 5-bromouracil, 5-chlorouracil, 4-thiouracil, 4-thiomethyluracil, cytosine, 5-methylcytosine, 5-bromocytosine, N-methylcytosine, N-phenylcytosine, N-benzylcytosine, N,N-dimethylcytosine, or guanosine; and Q is phenyl, substituted phenyl, benzyl, substituted benzyl, phenylacetylene, substituted phenylacetylene, styryl, substituted styryl, phenethyl, or substituted phenethyl. Formula Ia also includes mixtures of compounds of Formula Ia, including mixtures of enantiomers, diastereomers and/or other isomers in any proportion.

In one embodiment, the $P2Y_6$ receptor agonist compounds are $P^1$-(2',3'-benzylacetal uridine 5'-)$P^3$-(uridine 5'-)triphosphate; $P^1$-(2',3'-benzylacetal uridine 5'-)$P^3$-(cytidine 5')triphosphate; and $P^1$-(2',3'-benzylacetal guanosine 5'-)$P^3$-(uridine 5'-)triphosphate.

In another embodiment, the $P2Y_6$ receptor agonist compounds $P^1$-(2',3'-phenylacetal uridine 5'-)$P^3$-(uridine 5'-)

triphosphate; P$^1$-[2',3'-(phenylacetylene)acetal uridine 5'-]P$^3$-(uridine 5'-)triphosphate; and P$^1$-(2',3'-phenylacetal cytidine 5'-)P$^3$-(uridine 5')triphosphate.

A preferred P2Y$_6$ receptor agonist compound is P$^1$-(2',3'-benzylacetal uridine 5'-)P$^3$-(uridine 5'-)triphosphate. The structure is shown as below.

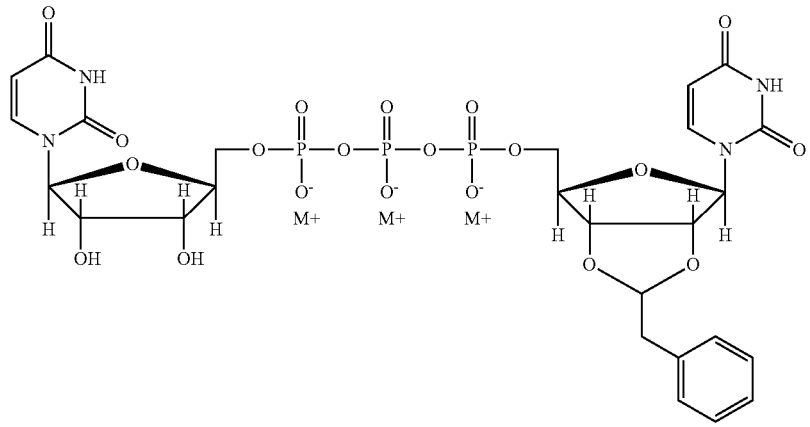

Pharmaceutical Formulation

The present invention additionally provides a pharmaceutical formulation comprising compounds of Formula I and a pharmaceutically acceptable carrier. Pharmaceutically acceptable carriers can be selected by those skilled in the art using conventional criteria. Pharmaceutically acceptable carriers include, but are not limited to, saline solution, aqueous electrolyte solutions, isotonicy modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation of the present invention provides an aqueous solution comprising water, suitable ionic or non-ionic tonicity modifiers, suitable buffering agents, and a compound of Formula I. In one embodiment, the compound is at 0.005 to 10% w/v, preferably 0.01-6% w/v, and the aqueous solution has a tonicity of 200-400 mOsm/kG and a pH of 4-9.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to systemic administration.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 3.5-5%, and more preferably 4.2-5% w/v.

The Formula I compounds can also be prepared into dry powder or equivalent inhalation powders using the well known art of super critical fluid technology. In such a case, the Formula I compounds is admixed with appropriate excipients and milled into a homogenous mass using suitable solvents or adjuvants. Following this, this mass is subjected to mixing using super critical fluid technology and suitable particle size distribution is achieved. The particles in the formulation need to be of a desired particle size range such that the particles can be directly inhaled into the lungs using a suitable inhalation technique or introduced into the lungs via a mechanical ventilator. Alternatively, a formulation can be designed such that the particles are large enough in size thereby offering sufficient surface area to dissolve completely in a suitable fluid when admixed together or to dissolve sufficiently enough prior to nebulization into the lungs.

In an attempt to prevent particle size growth and minimize crystal growth of the Formula I compounds, one embodiment is to include the use of spray-dried particles that have better aerodynamic properties than micronized material. This can be further extended to coat the surface of the hydrophilic molecule with one or more layers of hydrophobic material.

Another embodiment of this composition involves the preparation of freeze-dried or lyophilized preparation of the Formula I compounds. The lyophilized preparations can be used as is in the form of a dry powder inhaler or be admixed with other suitable adjuvants to be used as dry powder inhaler or as a nebulized preparation.

Routes of Administration

Any method of delivering the Formula I compound to the lumen of the lung, including local administration and systemic administration, is suitable for the present invention.

A preferred embodiment of the invention is localized administration. Local administration includes inhalation, topical application or targeted drug delivery. Methods of inhalation include liquid instillation, instillation as a pressurized fluid preparation via metered dose inhaler or equivalent, or inhalation of an aerosolized solution via nebulizer (preferred), inhalation of dry powder (more preferred), and directing soluble or dried material into the air stream during mechanical ventilation (also more preferred).

An example of targeted drug delivery is enclosure of the Formula I compound within a liposome, where the liposome is coated with a specific antibody whose antigen is expressed in the targeted lung tissue. Alternatively, the liposomal preparation can be designed in such a fashion wherein the core of the liposome contains the Formula I compound and the external surface of the liposomal preparation is comprised of cationically charged moieties which traverse the alveolar surface and bind to the alveolar surface.

It can be advantageous to construe a controlled delivery system of the Formula I compound since such an inhaled product targets the site of action, presents the compound of interest in small regimented quantities and reduces/minimizes any unwanted side effects. There are some limitations to the effectiveness of controlled release delivery systems since prolonged residence of some of the materials in the lungs can pose long term toxicity problems.

Another example of a delivery system includes nanoparticulate or microparticulate compositions of the Formula I compound. In such a case, the Formula I compound is formulated as a nanosuspension wherein the carrier is loaded with the Formula I compound; such a preparation is then filtered through a fine porous membrane or suitable filtering medium or is exposed to solvent interchanges to produce nanoparticles. Such nanoparticulate preparations can be freeze dried or held in suspension in an aqueous or physiologically compatible medium. The preparation so obtained can be inhaled by suitable means.

Another example of a suitable preparation includes a reconstitutable preparation. In this case, the Formula I compound is formulated in a preparation to contain the necessary adjuvant to make it physiologically compatible. Such a preparation can be reconstituted by addition of water for injection or suitable physiological fluids, admixed by simple agitation and inhaled using appropriate techniques described above.

This inhalation method involves an aerosol suspension of respirable particles comprising the active compound, which the subject inhales. The respirable particles can be liquid or solid, with a particle size sufficiently small to pass through the mouth and larynx upon inhalation. In general, particles having a size of about 1 to 10 microns, preferably 1-5 microns, are considered respirable.

For inhaled administration, surface concentrations of active compounds delivered can vary according to compounds; but are generally $1\times10^{-10}$-$1\times10^{-4}$ moles/liter, and preferably $1\times10^{-8}$-$1\times10^{-5}$ moles/liter.

The active compounds can also be administered systemically to target sites in a subject in need such that the extracellular concentration of a $P2Y_6$ agonist is sufficient to elicit chloride and water secretion and a stimulation of ciliary beat frequency. The term systemic as used herein includes subcutaneous injection, intravenous, intramuscular, intrasternal injection, intravitreal injection, infusion, inhalation, transdermal administration, oral administration, rectal administration and intra-operative instillation.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile injectable preparation can be a sterile injectable solution or suspension in a non-toxic acceptable diluent or solvent. Among the acceptable vehicles and solvents that can be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

Additional means of systemic administration of the active compound to the lungs of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds can also be systemically administered to the lungs of the subject through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs. The respirable particles can be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds to the lungs of the subject involves administering a liquid or a liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

For systemic administration, plasma concentrations of active compounds delivered can vary according to compounds; but are generally $1 \times 10^{-10}$-$1 \times 10^{-4}$ moles/liter, and preferably $1 \times 10^{-8}$-$1 \times 10^{-5}$ moles/liter.

Packaging

The selective $P2Y_6$ agonist compound can be packaged so as to allow a practitioner to formulate it into pharmaceutical compositions as needed. Alternatively, the pharmaceutical composition, itself, can be packaged, thereby requiring de minimus formulation by practitioner. In any event, the packaging should maintain efficacy and chemical and aesthetic integrity of therapeutic material or pharmaceutical composition to the extent reasonably possible.

Possible methods of packaging include blister packaging, packaging in unit dose vials, packaging in blow-fill-seal plastic vials, filling in pressurized canisters, packaging in a two compartment system wherein the contents of the two compartments are admixed by mechanical agitation prior to administration and the contents used within a specified period of time. Packaging the material by filling into a plastic vial whose contents can be easily opened, contents dispensed, and empty container disposed off to prevent re-use or contamination is deemed advantageous. The most preferred packaging method is packaging the formulation in a blister packaging system wherein the contents are held protected from heat, light, and other environmental extremes.

Where the therapeutic material is packaged for inhalation, the pharmaceutical composition can be packaged in aerosol spray canister or packaged for use with nebulizer or ventilator. This can be achieved by directly filling the container using the common techniques of cold filling or filling under a pressurized system or simply filling the product formulation under gravity feed in an aseptic environment. Depending on the nature of the final formulation, this can be achieved by a cold-filling technique wherein the composition is packaged in an aerosol canister under high pressure in a clean-room environment, preferably under aseptic conditions. Alternatively, if the composition is a simple solution, homogenous fluid, or well-mixed suspension product, the formulation can be filled into unit dose blow-fill-seal vials under a gravity feed or filled into blister packs wherein the formulation is filled into unit cavities and secured close with suitable foil or equivalent packaging to protect it from environmental extremes. This operation is preferred to be carried out under aseptic conditions, preferably under ambient or sub-ambient temperatures with little to no environmental extremes. It is desirable that such filling and packaging operations be conducted in relatively particulate free environments with minimal microbiological loads (especially absence of Pseudomonas and other similar pathogens) and be done with minimal exposure to direct human interface. The blister packaging can be done most optimally with cold fill packaging. The product compositions can be directly filled into the final container of choice by direct metered transfer (either gravimetrically or volumetrically) and secured close with appropriate closure systems.

The invention is illustrated further by the following examples that are not to be construed as limiting the invention in scope to the specific procedures described in them.

EXAMPLES

Example 1

Preparation of $P^1$-(2',3'-benzylacetal uridine 5'-)$P^3$-(uridine 5'-)triphosphate, ammonium salt Uridine 5'-diphosphate, tributylammonium salt ($UDP.NBu_3$)

Uridine 5'-diphosphate, disodium salt (UDP.2Na) was converted to the free acid by stirring with Dowex 50 H$^+$ or equivalent (5 g resin/g UDP.2Na) in water for 10 minutes. The resin was filtered and the filtrate was combined with tributylamine (1.5 eq.). The mixture was stirred vigorously for 15 minutes, such that the pH of the aqueous layer remained above 8. The solution was evaporated at <35° C., and the residue co-evaporated with dry N,N-dimethylformamide (3×), at <40° C. The residue was lyophilized overnight to a dry glassy foam.

Uridine 5'-monophosphate, tributylammonium salt ($UMP.NBu_3$)

Uridine 5'-monophosphate, free acid (UMP) was converted to the mono-tributylammonium salt by treatment with tributylamine (1.5 eq.) in water. Following solvent removal and co-evaporation with dry N,N-dimethylformamide, the product was lyophilized overnight to a constant weight.

$P^1$, $P^3$-di(uridine 5'-)triphosphate, triammonium salt $UMP.NBu_3$ (380 mg, 0.747 mmol, 1.1 eq) was dissolved in dry N,N-dimethylformamide (2 mL) and 1,1'-carbonyldiimidazole (242 mg, 1.49 mmol, 2.2 eq) added in a single portion. The solution was stirred at room temperature for 1 hour. $^{31}$P NMR indicated almost complete conversion to the imidazolide, and methanol (55 uL, 2 eq) was added to quench the excess of CDI. After 30 minutes stirring, $UDP.NBu_3$ (400 mg, 0.679 mmol, 1 eq) was added as a solid. The reaction mixture was stirred at 45° C. for 24 hours, with HPLC monitoring (Hamilton PRP-X100 column, 250×4.1 mm, 10 urn, gradient from water to 90% 1 M $NH_4HCO_3$/10% ACN over 30 or 60 minutes, 2 mL/min, monitor at 260 nm). At the end of the reaction HPLC indicated that the desired product constituted about 45% of the total nucleotide content. Water (500 uL) was added to quench any residual activated species and the solvents were evaporated at <40° C. and <5 mm Hg. The residue was reconstituted in water and the product was isolated by preparative HPLC. (Hamilton PRP-X100 column, 250×50 mm, 12-20 um, gradient from water to 90% 1 M $NH_4HCO_3$/ 10% ACN over 30 minutes; 100 mL/min, monitor at 260 nm). The yield of the title compound was 140 mg (27%).

$P^1$-(2',3'-benzylacetal uridine 5'-)$P^3$-(uridine 5')triphosphate, ammonium salt $P^1$, $P^3$-(uridine 5'-)triphosphate, triammonium salt (1.0 g, 1.31 mmol, 1 eq) was dissolved in 98% formic acid (5 mL) and phenylacetaldehyde, dimethylacetal (0.435 mL, 2.62 mmol, 2 eq) was added. The reaction mixture was stirred for three days at room temperature, at which point HPLC ($C_{18}$) indicated a 43% conversion to the desired monoacetal product, along with 14% of the undesired diacetal. The formic acid was removed as well as possible by evaporation, and the residue neutralized to pH 8 with 1 M sodium bicarbonate (30 mL). The aqueous solution was washed with ethyl acetate (2×20 mL) to remove excess aldehyde, and concentrated to 12 mL. The product was isolated via preparative HPLC (Nova-Pak $C_{18}$ column, 25×200 mm, gradient from 0.1 M ammonium acetate (pH 5.9) to methanol over 25 minutes, monitor at 260 nm). The yield of the title compound was 0.533 g. (47%).

$^1$H NMR (D$_2$O, 300 MHz) δ: 2.93 (d, 2H), 3.93-4.20 (m, 8H), 4.65 (m, 2H), 5.23 (t, 1H), 5.31 (d, 1H), 5.73 (m, 3H), 7.16 (m, 5H), 7.54 (d, 1H), 7.73 (d, 1H).

$^{31}$P NMR (D$_2$O, 121.47 MHz): −10.30 (d, 1P), −10.82 (d, 1P), −21.99 (m, 1P).

MW calculated for $C_{26}H_{31}N_4O_{20}P_3$ (MH$^-$) 811. found 811.3 by LCMS.

Example 2

Selectivity of UDP, UP$_3$U and Mono-Benzylacetal UP$_3$U

Human astrocytoma (1321N1) cells expressing P2Y$_1$, P2Y$_2$, P2Y$_4$, and P2Y$_6$ were grown to confluency in 96-well plates. Cells were loaded with a solution of Fluo-3 AM (2.5 µM final concentration) in an assay buffer consisting of 10 mM KCl, 118 mM NaCl, 2.5 mM CaCl$_2$, 1 mM MgCl$_2$, 20 mM HEPES, 10 mM glucose, pH 7.4. After a 60-minute incubation with Fluo-3 AM at 25° C., cells were washed and stimulated with serially diluted concentrations of compounds uridine 5'-diphosphate (UDP), P$^1$, P$^3$-(diuridine 5'-)triphosphate (UP$_3$U) or P$^1$-(2',3'-benzylacetal uridine 5'-)P$^3$-(uridine 5'-)triphosphate (mono-benzylacetal UP$_3$U). Intracellular calcium levels were monitored in each well simultaneously by measuring the changes in fluorescence intensity using the FLIPR (Molecular Devices Corp., Sunnyvale, Calif.). The results of this assay are presented in Table 1. Values for compounds UDP, UP$_3$U, and mono-benzylacetal UP$_3$U in Table 1 are presented as EC$_{50}$ values corresponding to the concentration of an agonist that produces 50% of the maximum possible response. Since mono-benzylacetal UP$_3$U has activity only at P2Y$_6$ receptors and requires the lowest concentration to elicit a response, these results illustrate that mono-benzylacetal UP$_3$U is a potent and selective agonist of P2Y$_6$ receptors. In a separate experiment, di-benzylacetal UP$_3$U (an analog of mono-benzylacetal UP$_3$U, where the two remaining hydroxyl groups are also substituted with a benzylacetal moiety, such that Y, Y', Z, and Z' are all OR), showed no response at P2Y$_6$.

TABLE 1

Potency and P2Y receptor selectivity.
EC$_{50}$ (µM)

| Compound | P2Y$_1$ | P2Y$_2$ | P2Y$_4$ | P2Y$_6$ |
|---|---|---|---|---|
| UDP | NR | 4.20 | 9.48 | 0.50 |
| UP$_3$U | NR | 13 | SR | 0.92 |
| mono-benzylacetal UP$_3$U | NR | NR | NR | 0.14 |

NR = No response
SR = Small response at 100 µM

Example 3

Chloride Secretion in Human Nasal Airway Cells

Induction of chloride secretion in vivo facilitates hydration of thickened airway mucus secretions in diseases where patients will benefit from mobilization and clearance of such secretions. Activation of an apical non-CFTR chloride channel induce efflux of chloride ions and water that help rehydrate the lung secretions (Boucher, U.S. Pat. No. 5,292,498 and Boucher, U.S. Pat. No. 5,635,160 and references therein).

Airway epithelial cells are dispersed and isolated from freshly excised human nasal surgical specimens (Yankaskas, et al., Am Rev Resp Dis 132, 1281-1287 (1985)). Confluent monolayers are cultured on permeable collagen matrix supports in F-12 hormone-supplemented medium (Wu, et al., Am Rev Resp Dis 132, 311-320 (1985)). Cells are incubated at 37° C. and grown to confluence. Development of transepithelial resistance is monitored to determine the formation of tight junctions between cells. After formation of tight junctions is confirmed, the matrix supports containing the cultures are mounted in modified Using chambers.

Cultured human airway epithelia are mounted in Using chambers with a submucosal bath of Krebs Bicarbonate Ringer, (KBR (in mM), 140 Na$^+$, 120 Cl$^-$, 5.2 K$^+$, 25 HCO$_3^-$, 2.4 HPO$_4^{2-}$, 0.4 HPO$_4^-$, 1.1 Ca$^{2+}$, 1.2 Mg$^{2+}$, and 5.2 glucose, pH 7.4). The luminal surface is bathed by KBr or by a high K$^+$, low CF Ringers ((in mM) 40 Na$^+$, 100 K$^+$, 4.5 Cl$^-$, 120 gluconate, 25 HCO$_3^-$, 2.4 HPO$_4^{2-}$, 0.4 HPO$_4^-$, 1.1 Ca$^{2+}$, 1.2 Mg$^{2+}$, and 5.2 glucose, pH 7.4).

Bioelectric properties including short-circuit current (I$_{SC}$), transpeithelial potential difference and resistance are monitored. I$_{SC}$ is measured with a digital voltmeter and plotted on a strip chart recorder. The open circuit potential is recorded periodically and conductance is monitored in the voltage clamp mode by the current deflection in response to a 10 mV voltage pulse. An increase in I$_{SC}$ is a measure of the activation of ion transport that leads to fluid transport and enhancement of mucocilliary clearance of the airways.

A stable baseline of I$_{SC}$ is recorded and amiloride (100 µM) is added to the solution bathing the apical surface to block the sodium absorption. The residual I$_{SC}$ measured under these conditions is a good approximation to chloride secretion (Boucher, et al., J. Clin. Invest. 78: 1245 (1986); Willumsen, et al., Am J Physiol 256: C226-C233; C1033-C1044; C1045-C1053 (1989)). After recording a stable baseline, a solution of a selective P2Y$_6$ agonist compound such as mono-benzylacetal UP$_3$U is added to the chamber bathing the apical surface of the epithelial culture. The change in I$_{SC}$ is recorded. Concentration-response curves are obtained by cumulative addition of higher concentrations of test compound in 0.5 log steps.

The P2Y$_6$ agonist compound increases the short circuit current (I$_{SC}$) in a dose-dependent manner, demonstrating an increase in chloride secretion and water, thus promoting the hydration of the airways.

Example 4

Ciliary Beat Frequency

The effects of a selective P2Y$_6$ agonist compound such as mono-benzylacetal UP$_3$U on ciliary activity are determined on individual human ciliated nasal epithelial cells using techniques described previously (Geary et al., Am J Physiol. 268, L1021-8 (1995); Morse et al. Am. J. Physiol. Cell Physiol. 280:C1485-497 (2001)). Briefly, epithelial cells are recovered from protease digests of human nasal turbinates, obtained from normal subjects and from patients with lung diseases such as cystic fibrosis, chronic bronchitis, primary ciliary dyskinesia and COPD. The cells are seeded into 12-mm Costar Transwell-Col cell culture supports at a density of 300,000 cells/cm² and incubated overnight in hormone-supplemented culture medium (Gray et al., *Am J Respir Cell Mol Biol* 14: 104-112 (1996)) at 37° C. in an atmosphere of air (5% $CO_2$), after which nonadherent cells are washed away to reveal small explants of the superficial epithelium as small clumps of ciliated cells that have attached to the substratum. These preparations are used within 4 days. Transwell-Col cell culture supports bearing epithelial explants are mounted in a chamber on the stage of an inverted microscope, superfused luminally, and warmed (35° C.) as described previously (Morse et al., 2001). The control superfusion and the serosal bathing solution is Krebs-Ringer bicarbonate (KRB) with the following composition: 125 mM NaCl, 5.2 mM KCl, 1.2 mM $MgCl_2$, 1.2 mM $CaCl_2$, 25 mM $NaHCO_3$, 10 mM TES, 5 mM glucose (pH 7.4 when gassed with 5% $CO_2$). The explanted, native ciliated cells are viewed by phase contrast microscopy using a Zeiss IM microscope (Carl Zeiss Inc., Thornwood, N.Y.) and 32× objective, and the image is monitored with a Dage 72 monochrome charge-coupled device video camera (Dage-MTI, Michigan City, Ind.). Ciliary beat frequency (CBF) is determined using a photosensor positioned over the image of an individual cell on the face of the video monitor to detect ciliary beating, as previously described (Morse et al., 2001). In all experiments, cultures are equilibrated with 1.5 h of superfusion with KRB. Each preparation is then subjected to two 10-min baseline and agonist stimulation periods, with variable concentrations of test compound, then with 100 µM UDP. Data are recorded every minute for the determination of CBF. A 30-min KRB washout period separated the test compound challenge from a subsequent second baseline period. After fast Fourier transformation analyses for each experiment, the resulting CBF data are normalized to the respective mean baseline CBF. For the test compound concentration-response study, the peak CBF is obtained and compared with that obtained with 100 µM UDP. The data are reported as the mean±S.E. of the peak response, relative to baseline. Cultures derived from the tissues of three or more patients are used.

The $P2Y_6$ agonist compound increases in a dose-dependent manner the beat frequency of cilia isolated from normal subjects and from patients with lung diseases such as cystic fibrosis, chronic bronchitis, primary ciliary dyskinesia and COPD, demonstrating improvements on mucociliary clearance.

Example 5

Mucin Secretion

Primary normal human tracheal/bronchial epithelial cells (donor-specific, nonsmoker), which are shipped cryopreserved in the presence of retinoic acid, are obtained from Clonetics (East Rutherford, N.J.; CC-2540). The cells are initially seeded on Transwell-Clear culture inserts (Corning-Costar 3460; Corning) and grown in bronchial epithelial growth medium (BEGM) (Clonetics; CC-3170 BEGM BulletKit base media, plus supplements). After 2 to 3 days in culture, cells are switched to air/liquid interface (ALI) culture conditions as has been previously described by Gray et al. (1996). The 17Q2 mucin antibody purified with a Protein G column (Pierce, Rockford, Ill.) from ascites fluid (University of California at Davis) is conjugated to alkaline phosphatase using the EZ-Link maleimide-activated alkaline phosphatase kit (Pierce).

Known amounts of a selective $P2Y_6$ agonist compound such as mono-benzylacetal $UP_3U$ are added to the apical surface of the cultures and incubated at 37° C. for 2 h. At the end of incubation period, mucin-containing cell supernatants are removed from the apical compartment and stored at −70° C. Estimation of mucin production is carried out using an antigen/antibody enzyme-linked immunoassay as described previously (Wright et al., *Am J Physiol* 271: L854-L861 (1996)).

Example 6

Tracheal Mucus Velocity

Prior to the study, approval of the Animal Research Committee, to assure the humane care and use of experimental animals is obtained. Adult ewes, 25 to 45 kg in weight, are restrained in an upright position in a specialized body harness adapted to a modified shopping cart. The heads of the animals are immobilized, and local anesthesia of the nasal passage is induced with 2% lidocaine. Following topical anesthesia of the nasal passages with 2% lidocaine solution, the sheep are nasally intubated with an endotracheal tube 7.5 cm in diameter (Mallinckrodt Medical Inc., St. Louis, Mo.), which has been shortened by 6 cm. The cuff of the tube is placed just below the vocal cords (verified by fluoroscopy) to allow for maximal exposure of the tracheal surface area. After intubation, the animals are allowed to acclimate for a period of 20 min before beginning measurements of Tracheal Mucus Velocity (TMV). During the course of the experiment, the inspired air is warmed and humidified using a Bennett humidifier (Puritan-Bennett, Lenexa, Kans.). To minimize possible impairment of TMV caused by inflation of the endotracheal tube cuff, the cuff is deflated throughout the study, except for the period of drug delivery. The sheep are periodically gavaged with tap water to avoid dehydration (Sabater et al., *J Appl Physiol* 87: 2191-2196 (1999)). TMV is measured in vivo by a roentgenographic technique as previously described (Sabater et al., *Am J Respir Crit Care Med* 154: 341-345 (1996), Sabater et al., *J Appl Physiol* 87: 2191-2196 (1999)). Between 10 and 12 radiopaque Teflon/bismuth trioxide disks, which are 1 mm in diameter, 0.8 mm thick, and 1.8 mg in weight, are insufflated into the trachea. A modified suction catheter connected to a source of continuous compressed air at a flow of 3 to 4 l/min is used to introduce the particles via the endotracheal tube. The catheter is maintained within the endotracheal tube only, so that no contact with the tracheal surface is made. The cephalad-axial velocities of the individual disks are recorded on videotape from a portable image intensifier unit. Individual disk velocities are calculated by measuring the distance traveled by each disk during a 1-min observation period. For each run, the mean value of all individual disk velocities is calculated. A collar containing radiopaque reference markers of known length is worn by the sheep during the study and used as a standard to correct for magnification effects inherent in the fluoroscopy unit.

After obtaining a baseline TMV, 4 ml aliquots of several concentrations of a $P2Y_6$ agonist compound such as mono-benzylacetal $UP_3U$ or placebo are administered by nebulization in sterile saline. The agents are delivered to the animals with a Pari LC Star nebulizer (Pari Respiratory, Richmond Va.), via free breathing. The nebulizer is driven by room air at a flow rate of 8 LPM, and the time to reach dryness is approximately 10 to 12 min. TMV is measured immediately after drug administration (0 h) and at 0.25, 0.5, 1, 2, 4, 6, and 8 h after treatment.

The $P2Y_6$ agonist compound increases the velocity of the cephalad axial displacement of radiopaque particles from the sheep trachea in a dose-dependent manner, demonstrating that the compound increases clearance of the airways.

Example 7

Treatment of Primary Ciliary Dyskinesia

A selective $P2Y_6$ agonist compound such as mono-benzylacetal $UP_3U$ is administered to patients diagnosed with primary ciliary dyskinesia (PCD) (verified by electron microscopy analysis of ciliary ultrastructure defect from nasal biopsy). The efficacy $P2Y_6$ receptor agonists is determined by measuring the clearance of inhaled radiolabeled particles from the lung by radionuclide scanning techniques using a gamma camera. Each subject inhales an aerosol of iron oxide labeled with Technetium $^{99}$m ($^{99}Tc-Fe_2O_3$). Subjects inhale the aerosol for approximately 5 minutes. Subjects are then seated in front of a gamma camera, and for the next 20 minutes the subjects randomly inhale either a saline control, or an effective concentration the $P2Y_6$ receptor agonist (0.1-100 mg/mL) for approximately 20 minutes. After this inhalation, subjects remain seated in front of the gamma camera for the next two hours to measure clearance of the radiolabeled iron oxide. The efficacy of the $P2Y_6$ receptor agonists in treating primary ciliary dyskinesia is demonstrated by an improvement in cough clearance of the $^{99}TC-Fe_2O_3$ as compared to the saline vehicle alone.

Example 8

Treatment of Chronic Bronchitis

A selective $P2Y_6$ agonist compound such as mono-benzylacetal $UP_3U$ is administered to patients diagnosed with chronic bronchitis (based upon the American Toracic Society definition: excess mucus production, occurring on most days for at least three months of the year for at least two successive years). The efficacy of the $P2Y_6$ receptor agonist is determined by measuring the clearance of inhaled radiolabeled particles from the lung by radionuclide scanning techniques using a gamma camera. Each subject inhales an aerosol of iron oxide labeled with Technetium $^{99}$m($^{99}Tc-Fe_2O_3$). Subjects inhale the aerosol for approximately 5 minutes. Subjects are then seated in front of a gamma camera, and for the next 20 minutes the subjects randomly inhale either a saline control, or an effective concentration of the $P2Y_6$ receptor agonist (0.1-100 mg/mL) for approximately 20 minutes. After this inhalation, subjects remain seated in front of the gamma camera for the next two hours to measure clearance of the radiolabeled iron oxide. Some studies include subjects that perform controlled coughs in this time period, and sputum is collected, weighed, and volume is recorded throughout the study, and stored for additional analysis of sputum rheology or iron content. Subjects repeat this procedure on subsequent days as appropriate to the number of doses under study. The efficacy of the inhaled $P2Y_6$ receptor agonists in treating chronic bronchitis is demonstrated by an improvement in mucociliary and/or cough clearance of the $^{99}TC-Fe_2O_3$ as compared to the saline vehicle alone.

Approximately 24 hours following each inhalation exposure, subjects are subjected to a 30-minute scan of residual radioactivity in the lung. During this time they sit continuously in front of the gamma camera.

Safety data is collected by monitoring heart rate, ECG, blood pressure, oxyhemoglobin saturation by pulse oximetry prior to, during and after inhalation for all dosing periods. All patients during all phases of the study are monitored for any adverse reactions during each dose period beginning with inhalation of study drug and ending after the 30 minute scanning at 24 hours.

Example 9

Treatment of Chronic Obstructive Pulmonary Disease (COPD)

A selective $P2Y_6$ agonist compound such as mono-benzylacetal $UP_3U$ is administered to patients diagnosed with Chronic Obstructive Pulmonary Disease (COPD), patients with airflow limitation that is not fully reversible. The airflow limitation is usually both progressive and associated with an abnormal inflammatory response of the lungs to noxious particles or gases. Patients have symptoms of cough, sputum production, or dyspnea (difficult or labored breathing), and/or a history of exposure to risk factors for the disease. The diagnosis is confirmed by spirometry (measurements of lung function and capacity) and clinical symptoms and signs, such as abnormal shortness of breath and increased forced expiratory time). The efficacy the $P2Y_6$ receptor agonists is determined by measuring the clearance of inhaled radiolabeled particles from the lung by radionuclide scanning techniques using a gamma camera. Each subject inhales an aerosol of iron oxide labeled with Technetium $^{99}$m ($^{99}Tc-Fe_2O_3$). Subjects inhale the aerosol for approximately 5 minutes. Subjects are then seated in front of a gamma camera, and for the next 20 minutes the subjects randomly inhale either a saline control, or an effective concentration of the $P2Y_6$ receptor agonist (0.1-100 mg/mL) for approximately 20 minutes. After this inhalation, subjects remain seated in front of the gamma camera for the next two hours to measure clearance of the radiolabeled iron oxide. Some studies include subjects that perform controlled coughs in this time period, and sputum is collected, weighed, and volume is recorded throughout the study, and stored for additional analysis of sputum rheology or iron content. Subjects repeat this procedure on subsequent days as appropriate to the number of doses under study. The efficacy of the inhaled $P2Y_6$ receptor agonists in treating COPD is demonstrated by an improvement in mucociliary and/or cough clearance of the $^{99}TC-Fe_2O_3$ as compared to the saline vehicle alone.

Approximately 24 hours following each inhalation exposure, subjects are subjected to a 30-minute scan of residual radioactivity in the lung. During this time they sit continuously in front of the gamma camera.

Safety data is collected by monitoring heart rate, ECG, blood pressure, oxyhemoglobin saturation by pulse oximetry prior to, during and after inhalation for all dosing periods. All patients during all phases of the study are monitored for any adverse reactions during each dose period beginning with inhalation of study drug and ending after the 30 minute scanning at 24 hours.

Although the invention has been described with reference to the presently preferred embodiments, it should be understood that various modifications could be made without departing from the scope of the invention.

What is claimed:

1. A compound selected from the group consisting of: $P^1$-(2',3'-phenylacetal uridine 5'-)$P^3$-(uridine 5'-)triphosphate; $P^1$-[2',3'-(phenylacetylene)acetal uridine 5'-]$P^3$-(uridine 5')triphosphate; $P^1$-(2',3'-phenylacetal cytidine 5'-)$P^3$-(uridine 5'-)triphosphate, and $P^1$-(2',3'-benzylacetal guanosine 5'-)$P^3$-(uridine 5'-)triphosphate.

2. The compound according to claim 1, which is $P^1$-(2',3'-phenylacetal uridine 5'-)$P^3$-(uridine 5'-)triphosphate.

3. The compound according to claim 1, which is $P^1$-[2',3'-(phenylacetylene)acetal uridine 5'-]$P^3$-(uridine 5'-)triphosphate.

4. The compound according to claim 1, which is $P^1$-(2',3'-phenylacetal cytidine 5'-)$P^3$-(uridine 5'-)triphosphate.

5. The compound according to claim 1, which is $P^1$-(2',3'-benzylacetal guanosine 5'-)$P^3$-(uridine 5'-)triphosphate.

* * * * *